(12) United States Patent
Wang

(10) Patent No.: US 8,421,680 B2
(45) Date of Patent: Apr. 16, 2013

(54) DIGITAL BROADCASTING ANTENNA STRUCTURE

(75) Inventor: Gary Wang, Taoyuan County (TW)

(73) Assignee: Yi Chang Hsiang Industrial Co., Ltd., Taoyuan, Taoyuan County (TW)

( * ) Notice: Subject to any disclaimer, the term of this patent is extended or adjusted under 35 U.S.C. 154(b) by 477 days.

(21) Appl. No.: 12/724,017

(22) Filed: Mar. 15, 2010

(65) Prior Publication Data

US 2010/0254482 A1    Oct. 7, 2010

(30) Foreign Application Priority Data

Apr. 3, 2009    (TW) .............................. 98205406 U

(51) Int. Cl.
*H01Q 9/04* (2006.01)

(52) U.S. Cl.
USPC .................... 343/700 MS; 343/846; 343/848

(58) Field of Classification Search .............. 343/700 R, 343/846, 700 MS, 848
See application file for complete search history.

(56) References Cited

U.S. PATENT DOCUMENTS

| | | | | |
|---|---|---|---|---|
| 4,907,011 A | * | 3/1990 | Kuo | 343/792.5 |
| 2008/0074327 A1 | * | 3/2008 | Noro et al. | 343/700 MS |
| 2008/0074328 A1 | * | 3/2008 | Noro et al. | 343/700 MS |

\* cited by examiner

*Primary Examiner* — Jacob Y Choi
*Assistant Examiner* — Scott Petersen
(74) *Attorney, Agent, or Firm* — Muncy, Geissler, Olds & Lowe, PLLC

(57) ABSTRACT

A digital broadcasting antenna structure includes a substrate having at least a first and a second face; a main antenna arranged on the first face; an amplifier arranged on the first face and electrically connected to the main antenna; a compensating unit arranged on the second face and electrically connected to the main antenna; a bandwidth modulating unit arranged on the second face and electrically connected to the compensating unit; and a grounding section arranged on the second face and electrically connected to the bandwidth modulating unit. The digital broadcasting antenna structure can receive digital broadcasting signals without being restricted to any specific receiving direction, and is applicable to low, intermediate and high frequency bands to therefore achieve the effects of miniaturization, high bandwidth and low return loss.

3 Claims, 3 Drawing Sheets

DIGITAL BROADCASTING ANTENNA STRUCTURE

CROSS-REFERENCE TO RELATED APPLICATIONS

This non-provisional application claims priority under 35 U.S.C. §119(a) on patent application No. 098205406 filed in Taiwan, R.O.C. on 3 Apr. 2009, the entire contents of which are hereby incorporated by reference.

FIELD OF THE INVENTION

The present invention relates to a digital broadcasting antenna structure, and more particularly to a digital broadcasting antenna structure that can receive digital broadcasting signals without being restricted to any specific receiving direction and is applicable to low, intermediate and high frequency bands to therefore achieve the effects of miniaturization, high bandwidth, and low return loss.

BACKGROUND OF THE INVENTION

It is known the current digital audio broadcasting (DAB) transmission technique is different from the conventional amplitude modulation (AM) and frequency modulation (FM) broadcasting techniques. By DAB, digital signals from satellites or terrestrial transmitting stations can be received via an antenna that is connected to a multimedia device, so as to achieve the purpose of broadcasting and improving the drawbacks in the conventional broadcasting techniques, including poor sound quality, easily interfered radio signals, and broadcasting quality easily affected by transmission power.

While the current DAB technique can improve the drawbacks in the conventional broadcasting techniques, it has the problems of having a bulky digital broadcasting antenna and being restricted to a fixed signal receiving direction. As a result, the current DAB technique has relatively poor signal receiving quality, insufficient bandwidth and high return loss.

It is therefore desirable to develop an improved digital broadcasting antenna structure capable of achieving the effects of high bandwidth and low return loss.

SUMMARY OF THE INVENTION

A primary object of the present invention is to provide a digital broadcasting antenna structure that includes a main antenna, an amplifier, a compensating unit, a bandwidth modulating unit and a grounding section specifically arranged on a substrate, and can therefore receive digital broadcasting signals without being restricted to any specific receiving direction and be applicable to low, intermediate and high frequency bands, so as to achieve the effects of miniaturization, high bandwidth, and low return loss.

To achieve the above and other objects, the digital broadcasting antenna structure according to the present invention includes a substrate having at least a first and a second face; a main antenna arranged on the first face; an amplifier arranged on the first face and electrically connected to the main antenna; a compensating unit arranged on the second face and electrically connected to the main antenna; a bandwidth modulating unit arranged on the second face and electrically connected to the compensating unit; and a grounding section arranged on the second face and electrically connected to the bandwidth modulating unit.

With these arrangements, the digital broadcasting antenna structure of the present invention can receive digital broadcasting signals without being restricted to any specific receiving direction, and is applicable to low, intermediate and high frequency bands to therefore achieve the effects of miniaturization, high bandwidth and low return loss.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
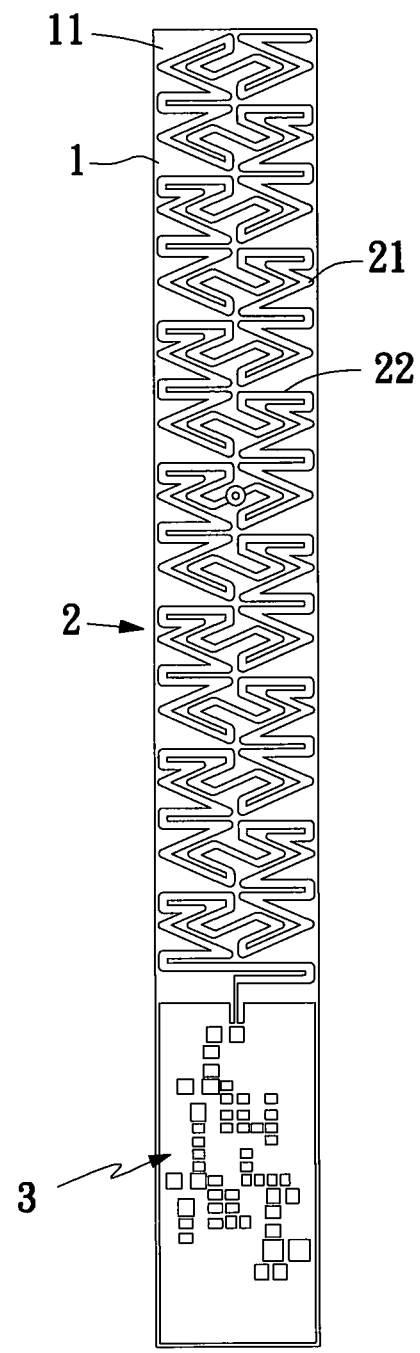
FIG. 1 shows a component layout on a first face of a digital broadcasting antenna structure according to a preferred embodiment of the present invention.
Figure 2:
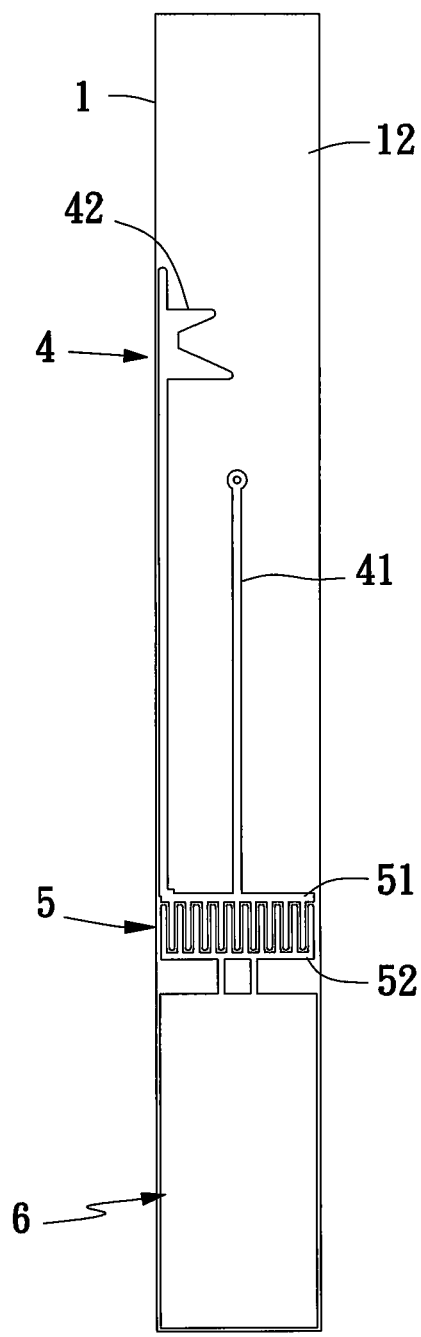
FIG. 2 shows a component layout on a second face of the digital broadcasting antenna structure according to the preferred embodiment of the present invention.
Figure 3:
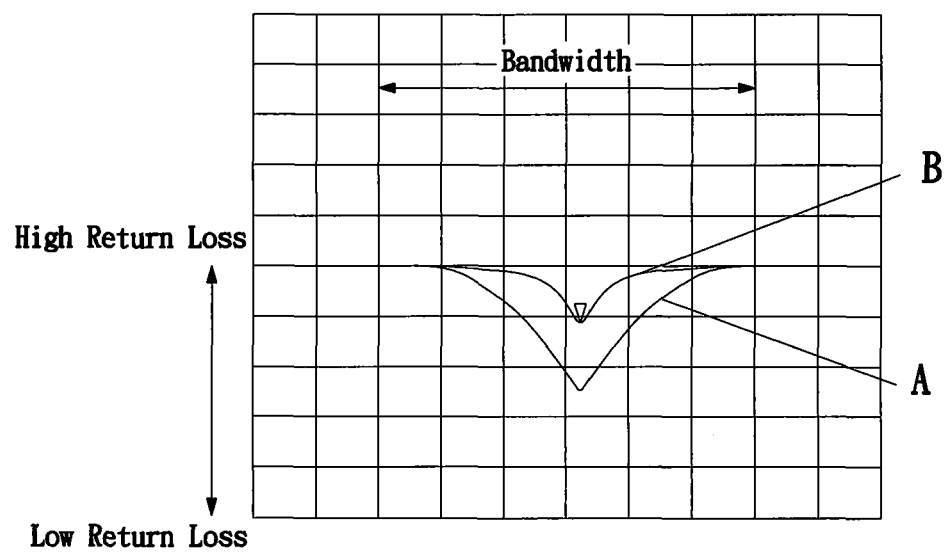
FIG. 3 is a graph comparing the characteristic of the digital broadcasting antenna structure according to the preferred embodiment of the present invention with that of a conventional antenna.

Please refer to FIGS. 1 and 2 that are component layouts on a first face and a second face, respectively, of a digital broadcasting antenna structure according to a preferred embodiment of the present invention; and to FIG. 3 that is a graph comparing the characteristic of the digital broadcasting antenna structure according to the preferred embodiment of the present invention with that of a conventional antenna. As shown, the digital broadcasting antenna structure according to the preferred embodiment of the present invention includes at least a substrate 1, a main antenna 2, an amplifier 3, a compensating unit 4, a bandwidth modulating unit 5, and a grounding section 6.

The substrate 1 includes at least a first face 11 and a second face 12.

The main antenna 2 is arranged on the first face 11 of the substrate 1, and includes a plurality of triangular sections 21 and a transversely extended electric-connecting section 22 located between any two longitudinally adjacent triangular sections 21 for electrically connecting the two adjacent triangular sections 21 to each other. The triangular sections 21 are so designed that the digital broadcasting antenna structure of the present invention can receive broadcasting signals without being restricted to any specific receiving direction.

The amplifier 3 is arranged on the first face 11 of the substrate 1 and electrically connected to the main antenna 2. The amplifier 3 is able to increase the stability of signal received by the main antenna 2. That is, the amplifier 3 can increase the gain of the signal.

The compensating unit 4 is arranged on the second face 12 of the substrate 1 and electrically connected to the main antenna 2. The compensating unit 4 includes a connecting section 41 connected to the main antenna 2 and a compensating section 42 connected to the connecting section 41. The main antenna 2 is extended through the substrate 1 to electrically connect to the connecting section 41. The connecting section 41 is downward extended from the joint with the main antenna 2 to enable increased bandwidth, and then turns to extend upward to connect to the compensating section 42 for reducing the return loss of the antenna. It is noted the compensating section 42 is arranged at a position without overlapping with the main antenna 2, so that the compensating section 42 does not hinder the main antenna 2 from receiving signals. Further, based on the condition of not overlapping with the main antenna 2, the compensating section 42 can be copper clad provided as large as possible in area. In the present invention, since the main antenna 2 presents a plurality of triangular sections 21, the compensating section 42 is designed corresponding to the main antenna 2 to be generally in the form of letter V.

The bandwidth modulating unit 5 is arranged on the second face 12 of the substrate 1 and electrically connected to the compensating unit 4. The bandwidth modulating unit 5 is used to modulate the bandwidth of the digital broadcasting antenna structure of the present invention. The bandwidth modulating unit 5 includes a first and a second comb-shaped section 51, 52, each of which has a plurality of parallelly spaced strips; the strips of the first comb-shaped section 51 and the strips of the second comb-shaped section 52 are arranged in staggered relation, and the first comb-shaped section 51 is connected to the compensating unit 4.

The grounding section 6 is arranged on the second face 12 of the substrate 1 and electrically connected to the second comb-shaped section 52 of the bandwidth modulating unit 5.

To use the digital broadcasting antenna structure of the present invention, first connect it to a related multimedia receiver device, and use the main antenna 2 to receive digital signals. With the particular arrangement of the amplifier 3, the compensating unit 4, the bandwidth modulating unit 5 and the grounding section 6 on the substrate 1, the digital broadcasting antenna structure of the present invention is advantageously miniaturized. When the present invention is used for receiving digital signals, the main antenna 2 is the component responsible for the receiving of the digital signals, and the received digital signal is amplified by the amplifier 3. When the main antenna 2 receives digital signals, the compensating unit 4, the bandwidth modulating unit 5 and the grounding section 6 cooperatively modulate the impedance of the received digital signals. Further, high bandwidth and low return loss can be achieved through the capacitance effect and topological effect of the main antenna 2 on the grounding section 6. When a network analyzer is used to measure the return loss of the antenna structure of the present invention in use, as can be seen from FIG. 3, a curve A indicating the return loss of the present invention is lower than a curve B indicating the return loss of a conventional antenna. Therefore, the main antenna 2 of the present invention can receive digital signals without being restricted to any specific receiving direction, and is applicable to low, intermediate and high frequency bands. The main antenna 2 is relatively longer when the present invention is applied in low frequency band, and is relatively shorter when the present invention is applied in high frequency band.

The digital broadcasting antenna structure of the present invention is novel and improved because the specific arrangement of the main antenna, the amplifier, the compensating unit, and bandwidth modulating unit and the grounding section on the substrate allows the present invention to receive digital signals without being restricted to any specific receiving direction and be applicable to low, intermediate and high frequency bands to thereby achieve the effects of miniaturized size, high bandwidth, and low return loss. The present invention is also industrially practical for use because products derived from the present invention would no doubt fulfill the current market demands.

The present invention has been described with a preferred embodiment thereof and it is understood that many changes and modifications in the described embodiment can be carried out without departing from the scope and the spirit of the invention that is intended to be limited only by the appended claims.

What is claimed is:

1. A digital broadcasting antenna structure, comprising:
a substrate including at least a first and a second face;
a main antenna being arranged on the first face of the substrate;
an amplifier being arranged on the first face of the substrate and electrically connected to the main antenna;
a compensating unit being arranged on the second face of the substrate and electrically connected to the main antenna wherein the compensating unit includes a connecting section connected to the main antenna and a compensating section connected to the connecting section, the main antenna is extended through the substrate to electrically connect to the connecting section, the connecting section is downward extended from the joint with the main antenna and turns to extend upward to connect to the compensating section, the compensating section is in a form of a letter V, and the compensating section is arranged at a position without overlapping with the main antenna;
a bandwidth modulating unit being arranged on the second face of the substrate and electrically connected to the compensating unit; and
a grounding section being arranged on the second face of the substrate and electrically connected to the bandwidth modulating unit.

2. The digital broadcasting antenna structure as claimed in claim 1, wherein the main antenna includes a plurality of triangular sections, and a transversely extended electric-connecting section located between any two longitudinally adjacent triangular sections to electrically connect the adjacent triangular sections to each other.

3. The digital broadcasting antenna structure as claimed in claim 1, wherein the bandwidth modulating unit includes a first and a second comb-shaped section, each of which has a plurality of parallelly spaced strips; the strips of the first comb-shaped section and the strips of the second comb-shaped section being arranged in staggered relation; the first comb-shaped section being connected to the compensating unit, and the second comb-shaped section being connected to the grounding section.

* * * * *